April 26, 1949. F. H. HOWARD Plant Pat. 834
ROSE PLANT
Filed May 14, 1947
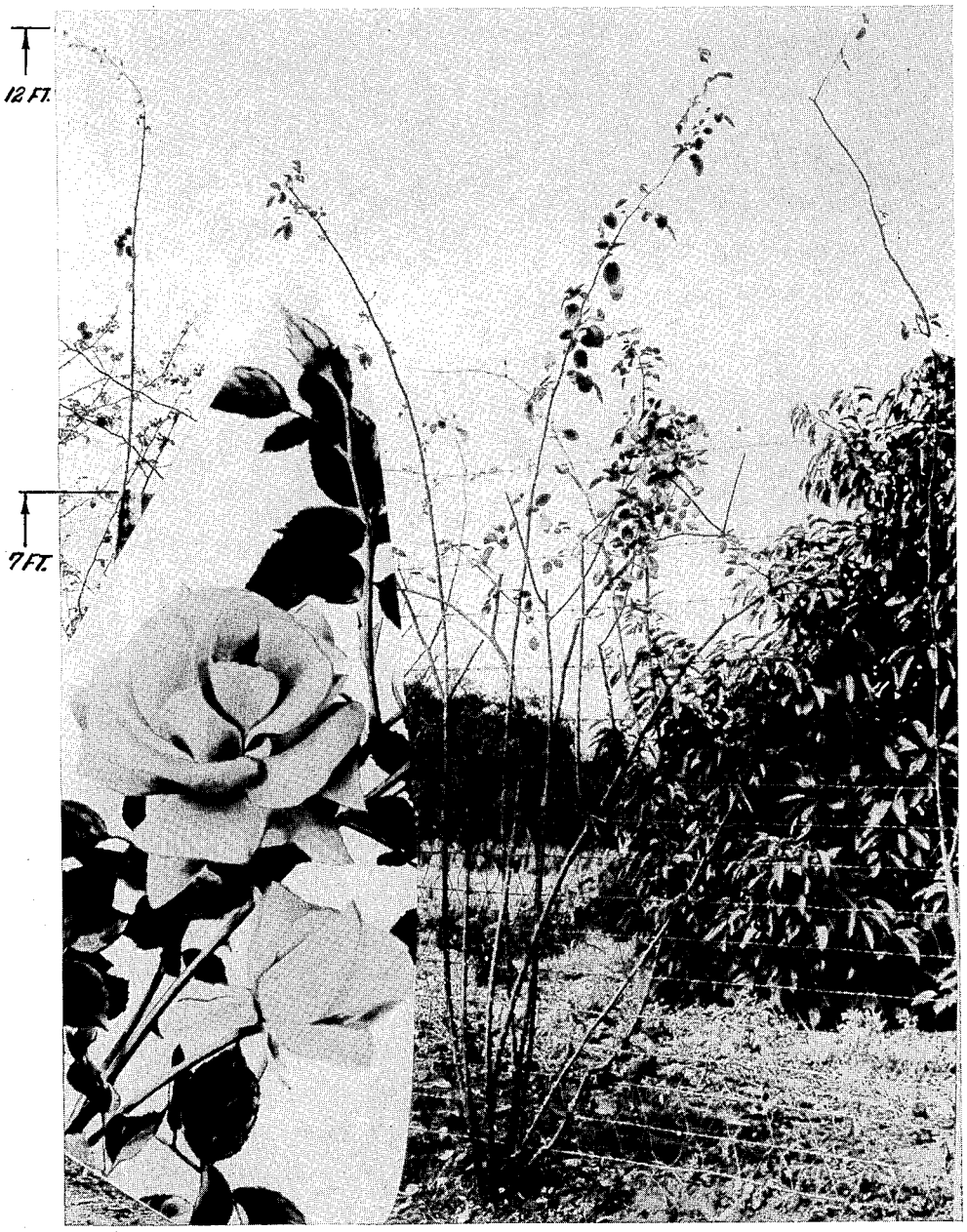
INVENTOR
Frederick Huber Howard
By Orville M. Kile
Plant Pat. Agt Patented Apr. 26, 1949

Plant Pat. 834

UNITED STATES PATENT OFFICE

834

ROSE PLANT

Frederick Huber Howard, Montebello, Calif., assignor to Howard & Smith, Montebello, Calif.

Application May 14, 1947, Serial No. 748,028

1 Claim. (Cl. 47—61)

My present discovery relates to a new and distinct variety of climbing hybrid tea rose plant, possessing most of the features of its parent plant, the Santa Anita (Plant Patent No. 539), from which it sported, except for its climbing ability and its accentuated size and strength of foliage, buds and blooms, and the issuance of more vigorous canes.

One of the outstanding features of this new variety is its freedom of bloom over an extended season. Although this is a feature of its parent, it is outstanding in climbing varieties. It begins blooming early in the spring and produces great quantities of bloom throughout the season, ceasing only when the period of natural winter dormancy arrives. The flowers are very large and of good form with petals well placed in the open flower, and the color is a uniform clear satiny pink. The plant is very mildew resistant and the flowers open well under the most adverse weather conditions and do not fade in hot weather.

The accompanying illustration shows a photographic reproduction of a plant of this new variety growing in my garden. The inset on the left is an illustration of a tight bud, a partly opened bud, an open flower, and portions of stems and foliage of this new variety.

The following description is similar to that found in Plant Patent No. 539, since much of the new plant is identical with its parent.

*The plant*

Growth: Climbing; very vigorous.

Disease and weather resistance: No mildew or other common rose disease has ever been found on this variety. Stands up well under hot and wet weather conditions. Hardy in the climate as found at Montebello, California.

Blooming habit: It is a profuse and continuous bloomer over an extended season from early spring to winter dormancy.

Stems: Very vigorous, heavy, stiff and strong. There are numerous medium-sized, sharp thorns, slightly downward-pointing and irregularly placed on the stem.

Foliage: Three to five leaflets which are broad with sharp apex and edges slightly serrated.

Abundant in quantity and leathery in texture. Medium to large in size and much heavier and stronger than in the bush form. Medium green on upper surface and lighter green on under surface.

*The flower*

Bud: Conical, long-pointed and large. Opens slowly and without "bullheading" under most adverse weather conditions. *Sepals* wide and short, usually simple. *Peduncle* strong and relatively short.

Bloom:

*Borne.*—Singly.

*Size.*—Large, measuring 4½ to 5½ inches in diameter when fully open.

*Form.*—High centered with petals well placed in loose formation.

*Petalage.*—From 24 to 30 in the fall season.

*Color.*—Uniform deep satiny pink which does not fade. Evenly distributed and approximately the same on both surfaces. Ridgway's Color Standards does not show this color but the nearest lies between Rose Color (Plate xii) and Spinel Pink (Pl. xxvi).

*Petals.*—Broad, with outer petals almost round. Deeply cupped.

*Fragrance.*—Moderate.

*Longevity.*—Very good.

*Reproductive organs.*—*Pistils* many and tightly bunched. *Styles* white at base, with upper portion red-tinged. *Stigma* greenish white. *Stamens* many, surrounding pistils. Slightly shorter than pistils. *Filaments* red-tinged. *Anthers* large and bright yellow.

Having thus disclosed my discovery, I claim: The new and distinct variety of hybrid tea rose plant herein disclosed, similar to its parent described in Plant Patent No. 539, except that it is characterized particularly by its large vigorous canes; its climbing ability; its larger, heavier and stronger foliage; and its larger sized buds and blooms.

FREDERICK HUBER HOWARD.

No references cited.